(12) United States Patent
Petit (10) Patent No.: US 8,795,283 B2
(45) Date of Patent: Aug. 5, 2014

(54) INSTRUMENT KIT FOR PERFORMING SPINAL STABILIZATION

(75) Inventor: Dominique Petit, Verton (FR)

(73) Assignee: Safe Orthopaedics SAS, Eragny sur Oise (FR)

( * ) Notice: Subject to any disclaimer, the term of this patent is extended or adjusted under 35 U.S.C. 154(b) by 2 days.

(21) Appl. No.: 13/253,247

(22) Filed: Oct. 5, 2011

(65) Prior Publication Data

US 2012/0031792 A1    Feb. 9, 2012

Related U.S. Application Data

(63) Continuation-in-part of application No. PCT/FR2010/000772, filed on Nov. 17, 2010, and a continuation-in-part of application No. PCT/FR2010/000880, filed on Dec. 28, 2010.

(30) Foreign Application Priority Data

Dec. 28, 2009   (FR) ...................................... 09 06369

(51) Int. Cl.
*A61B 17/88*   (2006.01)

(52) U.S. Cl.
USPC ....................................................... 606/86 A

(58) Field of Classification Search
USPC ......... 606/86 A, 914, 916; 403/286, 293, 381
See application file for complete search history.

(56) References Cited

U.S. PATENT DOCUMENTS

| | | | |
|---|---|---|---|
| 6,273,916 B1 | 8/2001 | Murphy | |
| 6,579,293 B1* | 6/2003 | Chandran | 606/64 |
| 2004/0138662 A1* | 7/2004 | Landry et al. | 606/61 |
| 2005/0192570 A1 | 9/2005 | Jackson | |
| 2006/0276803 A1 | 12/2006 | Salerni | |
| 2007/0078460 A1* | 4/2007 | Frigg et al. | 606/61 |
| 2007/0233079 A1* | 10/2007 | Fallin et al. | 606/61 |
| 2008/0262318 A1 | 10/2008 | Gorek et al. | |
| 2009/0022045 A1 | 1/2009 | Kondo | |
| 2009/0222045 A1 | 9/2009 | Gorek | |
| 2009/0240292 A1* | 9/2009 | Butler et al. | 606/86 A |
| 2010/0114179 A1* | 5/2010 | Moore et al. | 606/308 |
| 2012/0271365 A1* | 10/2012 | Daubs et al. | 606/86 A |

FOREIGN PATENT DOCUMENTS

| | | | |
|---|---|---|---|
| FR | 2668360 A1 | 4/1992 | |
| WO | 9622747 A1 | 8/1996 | |
| WO | 2005016183 A1 | 2/2005 | |
| WO | 2006002430 A2 | 1/2006 | |
| WO | 2007092870 A2 | 8/2007 | |
| WO | 2008097974 A2 | 8/2008 | |

* cited by examiner

*Primary Examiner* — Eduardo C. Robert
*Assistant Examiner* — Julianna N Harvey
(74) *Attorney, Agent, or Firm* — Bachman & LaPointe, P.C.

(57) ABSTRACT

A disposable surgical kit for fixing the vertebrae using a posterior or postero-lateral route has at least one pedicle screw or vertebral screw and an assembly tube cooperating with the screw. The assembly tube is composed of two independent rigid half-shells. Each of the half-shells has, on the inner face of its proximal end, a shoulder with a shape complementing a recess formed on each side of the screw head in order to permit the gripping or the release of the screw by spreading apart the distal ends of the half-shells The kit additionally has a retractable securing element for securing the half-shells. The retractable securing element has longitudinal fastening means designed as a dovetail for engaging with complementary slides formed in the rigid half-shells.

10 Claims, 7 Drawing Sheets

INSTRUMENT KIT FOR PERFORMING SPINAL STABILIZATION

BACKGROUND

1. Field of the Invention

The invention relates to an instrument kit for performing spinal stabilization by means of a bone-anchoring element of the screw type and using posterior or postero-lateral routes.

The instrument kit according to the invention is intended particularly, but not exclusively, for posterior surgical osteosynthesis of the lumbar, thoracic or even cervical spine, using minimally invasive routes or open surgery.

In cases of anatomical dysfunction of the vertebral column, bone anchors in the form of pedicle screws or vertebral screws are placed in the vertebrae, which are connected to each other by rod-type or plate-type connecting elements.

More particularly, the invention relates to the field of disposable instrument kits packed in a sterile state and comprising all the tools necessary for performing a surgical intervention for inserting pedicle screws without recourse to additional instruments.

2. Prior Art

The international application WO 2005/016183 is also known. The application describes a kit of implants of the vertebral plate and screw type combined with disposable instruments packed in a sterile state. Besides the disadvantage of providing only a single diameter and length of screw for the bone anchoring, this application describes only a single type of instrument, a screwdriver bar and its handle. This international application does not propose a technical solution for the design and production of instruments subjected to high mechanical stresses. Consequently, this sterile kit on its own does not allow a surgical intervention to be performed without also using traditional instruments, requiring re-sterilization after each intervention. The reason is that it is difficult to reconcile the constraints of low production costs, a necessary condition for disposable instruments, and the qualities of mechanical strength, a necessary condition for instruments subjected to high stresses during their use by the surgeon.

In the prior art, a spinal device described in US patent application US2004/138662 has been proposed, comprising a slotted tube with, at its proximal end, a means for fastening a screw. The distal end is articulated by a hinge, making it possible to move the proximal ends of the two branches apart in order to free the head of the screw and permit the withdrawal of the tube after implantation of the screw.

Within the meaning of the present application, "proximal" signifies nearest to the site of spinal intervention, and therefore the end farthest from the operating surgeon, and "distal" signifies the end remote from the spinal zone and therefore accessible by the operating surgeon. The screw is fixed on the proximal end.

International patent application WO2007/092870 describes another solution for a spinal device formed by a tube with pincers at its proximal end.

US patent application US2005/0192570 proposes another embodiment of a spinal device composed of a tube with a longitudinal slit and a slotted proximal end permitting the fastening of a screw and release by spreading apart of the proximal end.

The solutions in the prior art proposing that the screw be released by spreading apart the proximal ends of the screw-supporting tube are not satisfactory since they require a sufficient space in the zone surrounding the screw in order to permit disconnection. However, in this zone, the presence of the bone part often limits the available space and may lead to difficulties in releasing the tube from the head of the screw.

Moreover, the forces that need to be transmitted for radially disengaging the proximal end of the tube from the head of the screw are substantial and involve maneuvers that are not especially ergonomic at a distance. The release of the screw involves actions that can also lead to the operating site being concealed during this delicate phase of the intervention.

US patent applications US2008/0262318 and US2009/022045 describe a tissue retractor made of a flexible plastic material, and a means for withdrawing the retractor by rupture of a weakened zone provided in the proximal part of the retractor. The retractor has two flexible branches joined at their proximal end by a zone of permanent connection to the head of the screw. The distal ends of the two branches are free to allow a transverse force to be exerted, with the object of ensuring a pressure tending to spread apart the margins of the muscle tissues. The object is to allow the surgeon to view the zone of implantation of the rod on the pedicle screws without introducing an additional retractor.

Between the distal end of the two flexible branches and the zone of permanent connection to the head of the screw, a weakened zone is provided for disconnecting the screw from the two branches at the end of the intervention.

This retractor from the prior art poses a risk of unintentional rupturing of the weakened zone when a force is applied to the two flexible branches in order to spread the tissues apart. The compromise between the flexibility allowing the two branches to be spread apart at an angle and the required rupture for withdrawing the instrument is delicate. If the weakened zone is too strong, the surgeon may certainly apply considerable forces to the margins of the incision, but he will have to apply excessive and sometimes invasive forces when disconnecting the retractor from the screw. If it is not strong enough, the surgeon risks breaking the retractor inadvertently during the intervention.

Moreover, the transverse forces to apply for spreading the tissues apart impact axially on the screw, because of the connection of the screw and the branches of the retractor.

Moreover, this device does not allow the whole surgical intervention to be performed, and in particular it does not provide the instrumentation for placement of the rod, and then of the element for blocking the rod on the pedicle screw.

SUMMARY OF THE INVENTION

The object of the invention is to overcome these disadvantages by making available a complete disposable kit for inserting pedicle screws and associated spinal stabilization rods.

To this end, the invention relates in its most general sense to a disposable surgical kit for fixing the vertebrae using a posterior or postero-lateral route, said surgical kit comprising at least one pedicle screw or vertebral screw, and an assembly tube cooperating with said screw, wherein the assembly tube is composed of two independent rigid half-shells, and each of the half-shells has, on the inner face of its proximal end, a shoulder with a shape complementing a recess formed on each side of the screw head, in order to permit the gripping or the release of said screw by spreading apart the distal ends of said half-shells. The kit additionally comprises a retractable securing element for securing said half-shells which retractable securing element has longitudinal fastening means designed for engaging with complementary slides formed in the rigid half-shells.

This solution makes it possible to disconnect the screw and withdraw the tube after the implantation of the screw without the need for a radial space to be available around the proximal end. This release is effected by spreading the distal ends of the tube apart, which is possible with the device according to the invention by pivoting each of the rigid half-shells with respect to the zone of fastening of the head of the screw. This spreading apart of the distal end also makes it possible to clear the view of the proximal zone of placement of the screw.

Preferably, the assembly tube is pre-mounted on the screw, and the assembly tube is detachable from the screw.

Advantageously, the kit is supplied in a sealed package for sterile packaging comprising at least the bone-anchoring element and the pre-mounted assembly tube.

According to one variant, the assembly tube has a longitudinal opening leading into the proximal part of the bone-anchoring element for the passage of the connecting element.

Preferably, the assembly tube has a longitudinal opening leading into the proximal part of the bone-anchoring element for the passage of the connecting element.

Preferably, the securing element is pre-mounted on a blocking element for blocking the rod with respect to the screw, the internal diameter of the assembly tube permitting the passage of the blocking element for blocking the connecting element on the bone-anchoring element.

Advantageously, the kit comprises an ancillary passing through the assembly tube and having an end pre-mounted on the screw for transmission of a screwing torque.

Preferably, the half-shells have, at the opposite end from the screw, at least one threaded or internally threaded zone for joining the half-shells parallel to each other by way of a ring.

According to one variant, the two half-shells have, in their joined parts, a tenon-and-mortise positioning means.

According to one alternative, the kit has a ring provided with a bayonet-type formation for engaging on stubs formed on the two half-shells.

Advantageously, the blocking element support tube has an internal shape permitting the passage of a screwdriver.

Preferably, all the components are disposable.

BRIEF DESCRIPTION OF THE DRAWINGS

Other objects and advantages of the invention will become clear from the following description provided with reference to the attached drawings, in which.

DETAILED DESCRIPTION OF THE PREFERRED EMBODIMENT(S)

Figure 1:
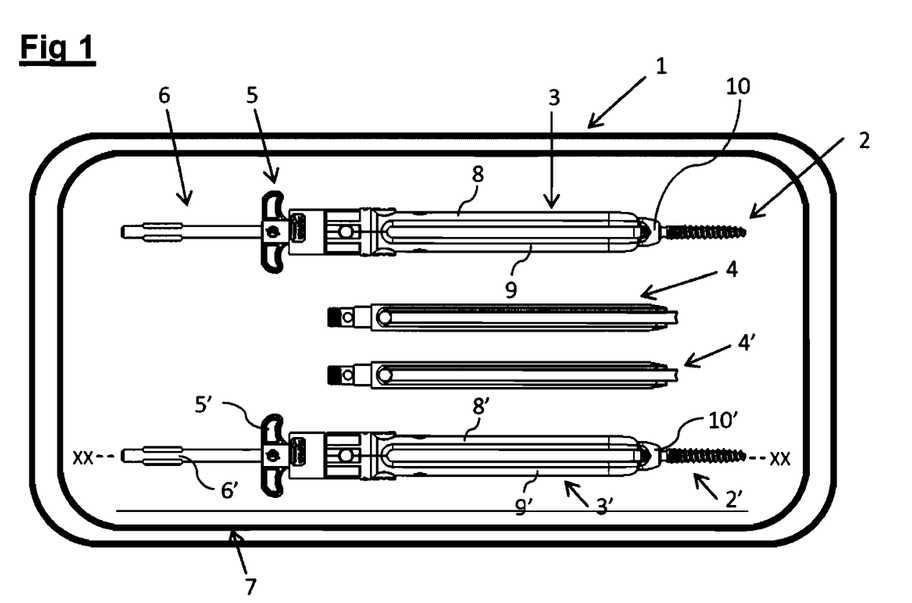
FIG. 1 shows a schematic view of an instrument kit according to one embodiment of the invention.

FIG. 1 describes a kit (1) for performing a surgical intervention for spinal stabilization. The kit (1) comprises:
two screws (2, 2') pre-mounted securely on assembly tubes (3, 3'),
two securing elements (4, 4') designed for placing the connecting rod on the bone-anchoring element and comprising blocking elements (41) pre-mounted on said securing tubes (3, 3'). The securing tubes (3, 3') comprise a pre-mounted holding wing (5, 5') and pre-mounted screwdriver (6, 6').

The assembly tube (3, 3') is composed of two half-shells (8, 9) of semi-tubular section and of complementary shapes. The screw (2, 2') is fastened to the proximal end of the two half-shells (8, 9; 8', 9') by virtue of an arrangement described below.

The securing element (4) is composed of a hollow rigid component that can be slid inside an assembly tube (3, 3'). It has an outer cross section complementing the inner cross section of the assembly tube (3, 3'). When the securing element (4, 4') is placed in the assembly tube (3, 3'), it secures the half-shells (8, 9) and keeps them in a position parallel to each other so as to form a rigid tube and to ensure locking of the fastening of the screw (2).

The securing element (4, 4') can be traversed by a tool, for example the rod of a screwdriver, in order to screw the tightening plug of a plug ensuring the blocking of a correcting rod into the hollow provided for this purpose in the head (10, 10') of the screw (2, 2').

All of the tubes/screwdrivers/handles/screws and tubes/blocking elements are arranged in a disposable sealed package (7) for sterile packaging.

The arrangement thus packaged forms a bone-anchoring kit providing two bone-anchoring elements and two blocking elements for performing spinal stabilization with the aid of a connecting rod.

Of course, bone-anchoring kits can obviously be provided that comprise not just one bone-anchoring element but several bone-anchoring elements and several blocking elements pre-mounted on tubes, as has been described above, without thereby departing from the scope of the invention.

Figure 2:
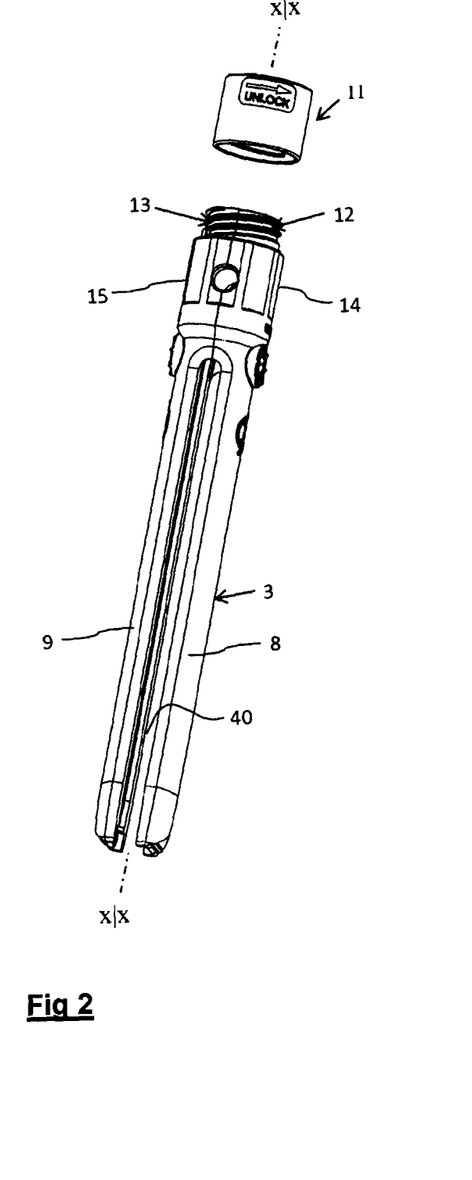
FIG. 2 shows a schematic view of the assembly tube and of the ring, the ring being shown not mounted on the assembly tube.
Figure 2A:
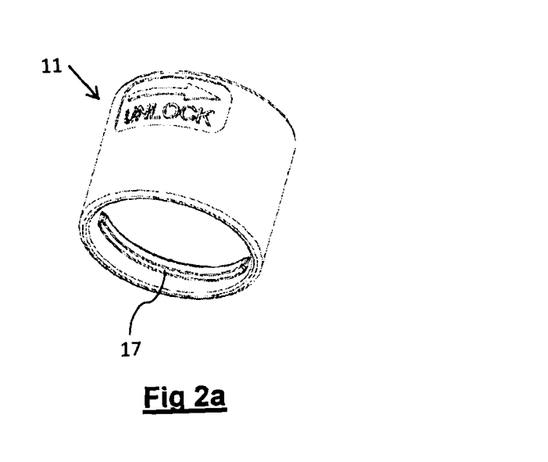
FIG. 2a shows a bottom view of the ring from FIG. 2.
Figure 3:
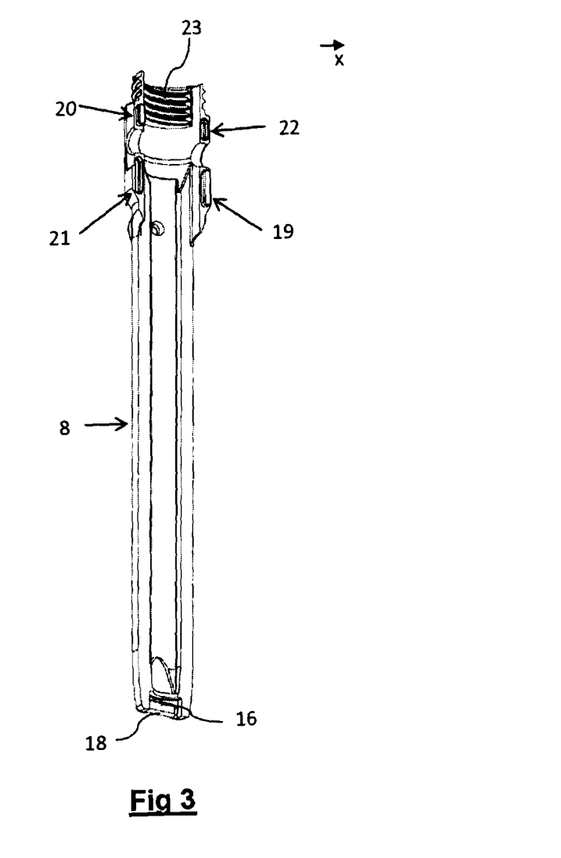
FIG. 3 shows a view of an assembly half-shell.

FIGS. 2, 2a and 3 show views of a tube (3) composed of two half-shells (8, 9) and of a holding ring (11), which is shown on an enlarged scale in FIG. 2a. The ring (11) has a cylindrical shape, with a thread (17) formed on its inner face.

The two half-shells (8, 9) are independent and can be joined together to form a tube with two parallel branches. To keep these two half-shells (8, 9) joined together, a ring (11) is screwed onto the end remote from the screw (2). For this purpose, each half-shell (8, 9) has a threaded zone (12, 13) formed in such a way as to ensure a continuous external thread when they are joined together. This thread (12, 13) complements the thread (17) provided on the inner surface of the ring (11).

The two half-shells (8, 9) are absolutely identical.

This threaded zone (12, 13) is continued by a zone (14, 15) comprising facets for engagement of a tool that is used to prevent rotation of the tube during the tightening of the plug with the aid of a screwdriver passing through this tube.

The distal part of each of the half-shells has a tenon (19, 20) on one side and a mortise (21, 22) on the other side, these being arranged in such a way as to permit a precise positioning of the two half-shells in assembled mode. It also has an internal thread (23) designed to receive the complementary thread of an accessory tool, for example a tool for pushing the rod into the head (10) of the screw (2).

This joining-together of the two half-shells by complementary tenon and mortise arrangements mechanically strengthens the unit as a whole and thereby avoids any risk of the two half-shells moving apart or becoming detached under high stresses and provides greater strength of the unit in flexion and torsion.

On its inner face, the proximal end of the half-shells (8, 9) has a recess (16) defining a protruding shoulder with a ridge (18) extending the transverse plane perpendicular to the center axis of the tube (3). When the two half-shells (8, 9) are joined, their ridges (18, 18') are parallel and spaced apart by a distance corresponding to the distance between the recesses (28, 28') provided on the screw head (10).

Figure 14:
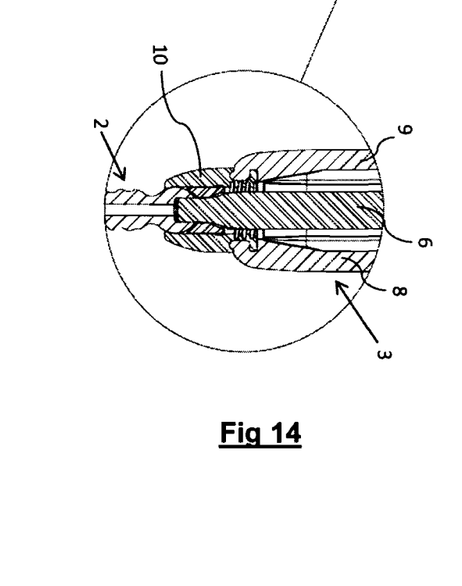
FIGS. 14 and 15 show a detailed view of the proximal end and of the distal end, respectively, of the tube illustrated in FIG. 13.

This configuration permits a connection to the head (10) of the screw (2) shown on an enlarged scale in FIG. 14.

Figure 4:
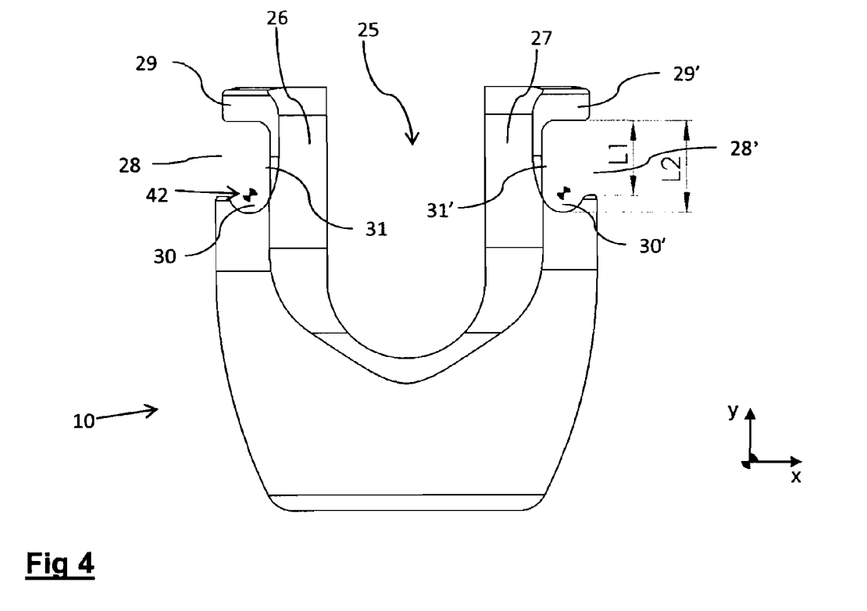
FIG. 4 shows a detail of the head of the screw.

The head (10) has a socket formed by a hemispherical seat in which the spherical end of the bone screw will be positioned. This spherical end has, in a known manner, a recess with a shape complementing the end of a screwdriver, for example a six-lobed recess. The screw is thus articulated with axial rotation and tilting with respect to the central longitudinal axis.

The head (10) has a hollow tubular shape with a U-shaped passage (25) permitting the engagement of an intervertebral connecting rod. It has an internal thread permitting the blocking of the screw head and rod with the aid of a blocking element, in particular a screwable plug.

The head (10) has, on each of the tile-shaped flanks (26, 27), a seat (28, 28') delimited in its upper part by a shoulder (29, 29') and in its lower part a groove (30, 30'), having a center of rotation (42), and by a bottom (31, 31').

This receiving cavity having an internal volume with a height L2 greater than the width L1 of the inlet aperture. This difference in size makes it possible for the shoulder (18) provided at the end of a half-shell (8, 9) to be engaged by a tilting movement. The half-shell (8, 9) is presented at an angle of about 15° with respect to a longitudinal center plane, which permits the introduction of the shoulder into the cavity (28). The half-shell (8, 9) is then repositioned parallel to the longitudinal plane, which causes the shoulder (18) to anchor in the cavity (30) by rotation of the proximal end of the half-shell (8, 9) with respect to the center of rotation (42).

In this position, the screw head (10) is locked with respect to the tube (2) and cannot be withdrawn by rotation with respect to the center of rotation (42) followed by axial traction. Moreover, the connection between each of the half-shells (8, 9) with respect to the corresponding cavities of the screw head ensures a rigid connection between the tube (2) and the screw head (10), prohibiting any relative movement between these two components.

When the two half-shells (8, 9) are held together by the ring (11), they form a rigid unit.

By contrast, when the ring is withdrawn, the half-shells (8, 9) are freed and can tilt with respect to the tangential axis defined by the rolling of the shoulder of the half-shell (8, 9) on the internal envelope of the cavity (28). Each of the half-shells then has a degree of freedom in rotation and can be oriented in a position parallel to the central longitudinal plane, and an inclined position in which the half-shell of the order of 15° with respect to this central longitudinal plane, before disconnection. Each half-shell (8, 9) can be tilted independently. This configuration makes it possible in particular to use the half-shells to apply pressure to the margins of the incision in the body tissues and also to clear the view of the zone of intervention on the vertebra. The half-shells thus act in the manner of a tissue retractor, with anchoring on the head (10) of the screw.

Advantageously, the ring (11) has an external diameter smaller than the nominal diameter of the recess when the two half-shells (8, 9) are in position in order to form the tube. This specific dimensioning of the ring (11) has the aim of permitting the passage of the perpendicular holding element for its position in the area of the recess.

Figure 5:
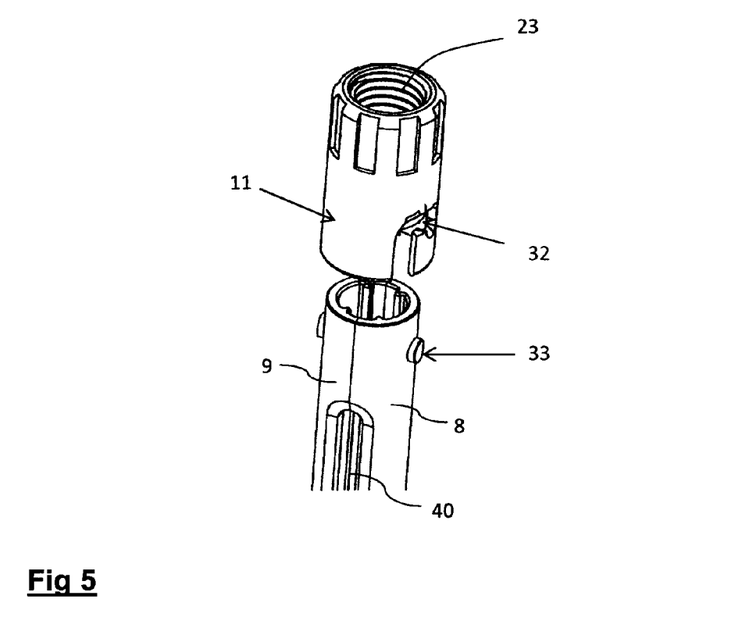
FIG. 5 shows a view of a ring variant with bayonet assembled on the two half-shells forming the assembly tube.

FIG. 5 shows a view of a variant of the arrangement of the ring on the two half-shells forming the assembly tube.

According to this variant, the ring is mounted on the two half-shells not by a threaded arrangement, but by a bayonet. The cutting (32) of the bayonet will engage on shoulders (33) projecting from the surface of each of the half-shells.

Figure 6:
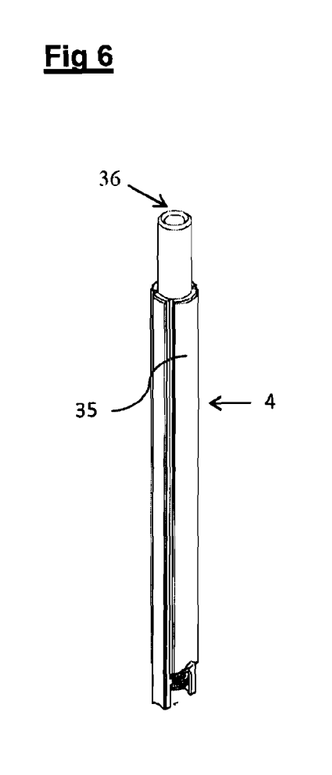
FIG. 6 shows the retractable securing element.

FIG. 6 shows the retractable securing element (4). It is formed by a hollow profiled component presenting a guide path (35, 35') of substantially trapezoid cross section of the "dovetail" type engaging in a a longitudinal guiding groove of complementary shape provided inside each half-shell (see FIG. 8).

The securing element (4) has two longitudinal slides (80, 90) with a cross section complementing the cross section of the guide paths (35, 35') provided on the half-shells (8, 9). These two slides (80, 90) are diametrically opposite and have a distal flare forming an abutment preventing insertion of the element (4) in the wrong direction.

Figure 7:
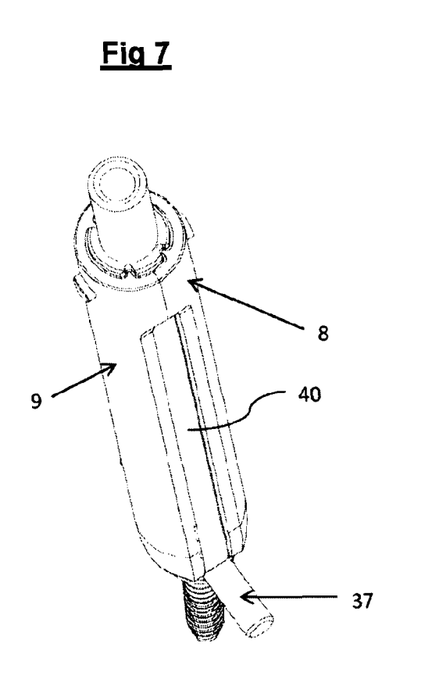
FIG. 7 shows the blocking element support tube inserted into the two half-shells forming the multi-function assembly tube.
Figure 8:
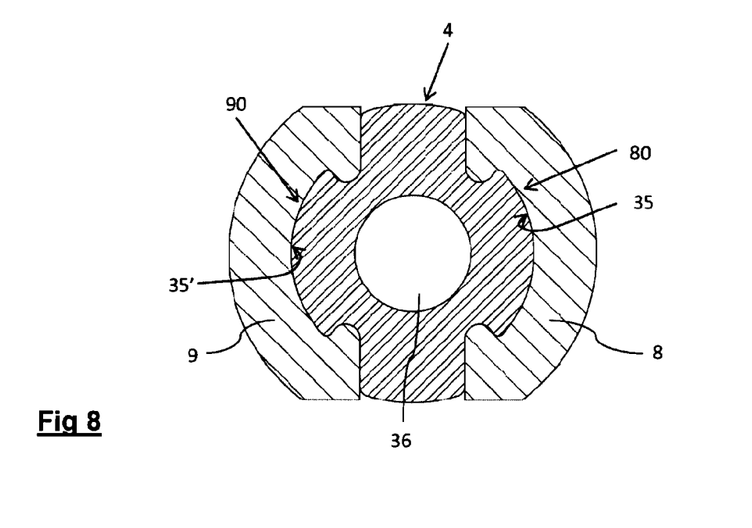
FIG. 8 shows a cross section through the device shown in FIG. 7.

When the two dovetail-shaped guide paths (35, 35') of the securing element (4) are engaged in one another in the assembled position of the half-shells, this element (4) locks the positioning of said half-shells and stabilizes the tube (2), as shown in FIGS. 7 and 8.

These complementary dovetails (35, 35') between the two half-shells (8, 9) and the support tube of the securing element (4) mechanically strengthen the unit and thereby avoid any risk of the two half-shells moving apart or becoming detached under high stresses and provide greater strength of the unit in flexion and torsion.

This securing element (4) is hollow and has a longitudinal channel (36) permitting the passage of the rod of a screwdriver for applying a screwing torque to the plug locking the rod/screw/screw head unit.

Figure 9:
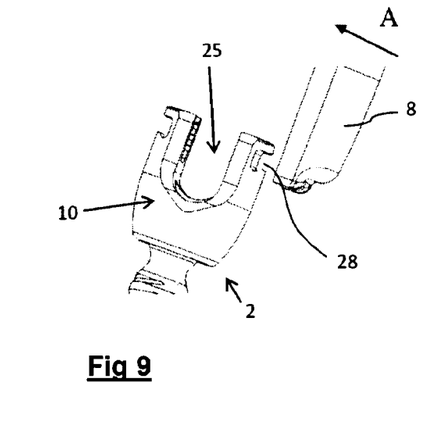
FIGS. 9 and 10 show the connection between the bone-anchoring element and the assembly tube.
Figure 10:
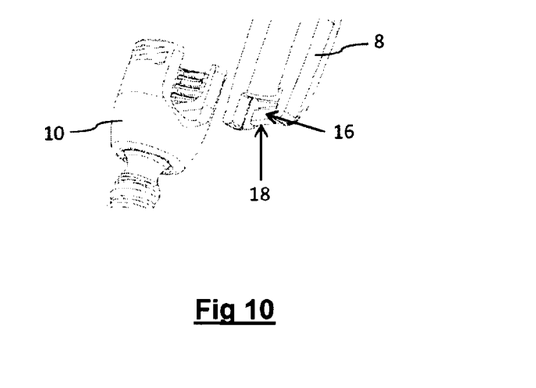

FIGS. 9 and 10 show the connection between the bone-anchoring element and the multi-function assembly tube.

The screw head (10) has a general cylindrical shape, with a hemispherical bottom for receiving the upper end of the screw and permitting a rotary tilting of the screw in the manner of a ball-and-socket type connection. This configuration is well known in the prior art.

The cylindrical upper part has two cutouts forming a channel (25), of which the width corresponds substantially to the width of an intervertebral connecting rod.

The screw head (10) has, on its outer surface, two recesses (28) formed on each side of the U-shaped channel (25). The recess is composed of a channel and of an inner seat (30). In this configuration, the assembly tube (3) is composed of two half-shells (8, 9). The female form of the recess on the head (10) of the screw (2) is reproduced in male form on the proximal ends of the half-shells (8, 9). Advantageously, the inner female form of the head (10) of the screw (2) is reproduced in outer male form (16) at the proximal end of the two half-shells (8, 9), in order to secure in all senses (except that of rotation with (42) as center of rotation).

More particularly, each half-shell (8, 9) has, at the proximal end, a cavity with a shape complementing the shape of one of the branches of the head (10) of the screw (2). Thus, when the two half-shells (8, 9) are mounted on the head (10) of the screw (2), the branches of the latter are confined in the cavities formed on each of the proximal ends of the half-shells, and the wall that delimits each cavity substantially "matches" the outer surface of the branches of the head (10) of the screw (2). Advantageously, the cavity of each proximal end has a shoulder formed in such a way that, when the proximal ends are placed on the head (10) of the screw (2), the shoulder engages in the recess formed on the screw head. In the embodiment illustrated, the recesses are formed at the upper end of the head (10) of the screw (2).

Figure 11:
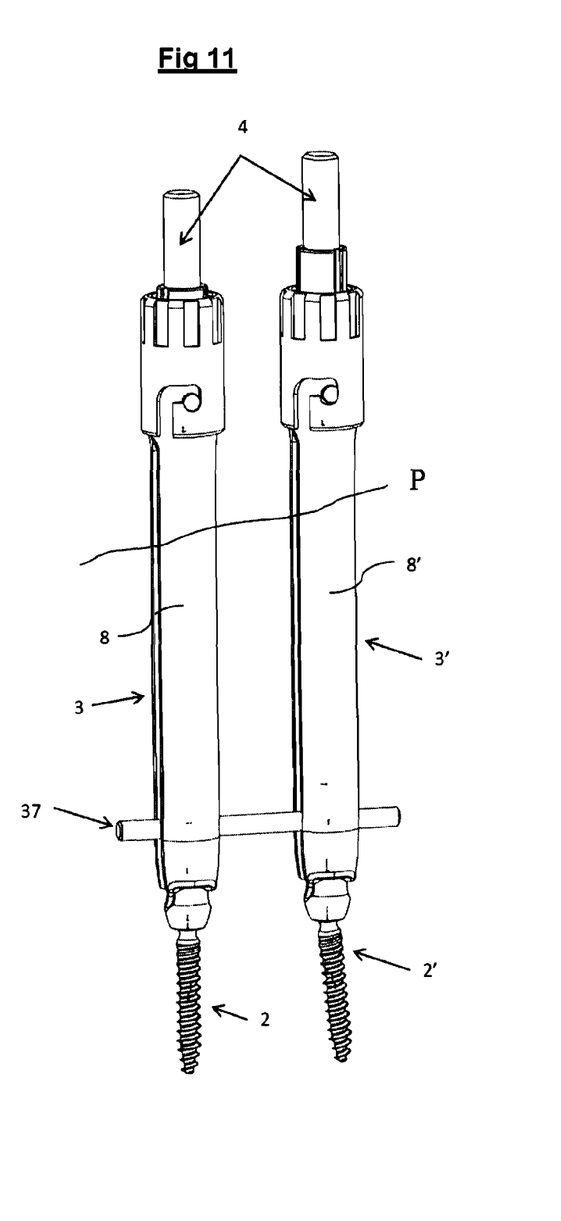
FIGS. 11 and 12 show the different operating steps involved in fitting the intervertebral connecting rod in place.
Figure 12:
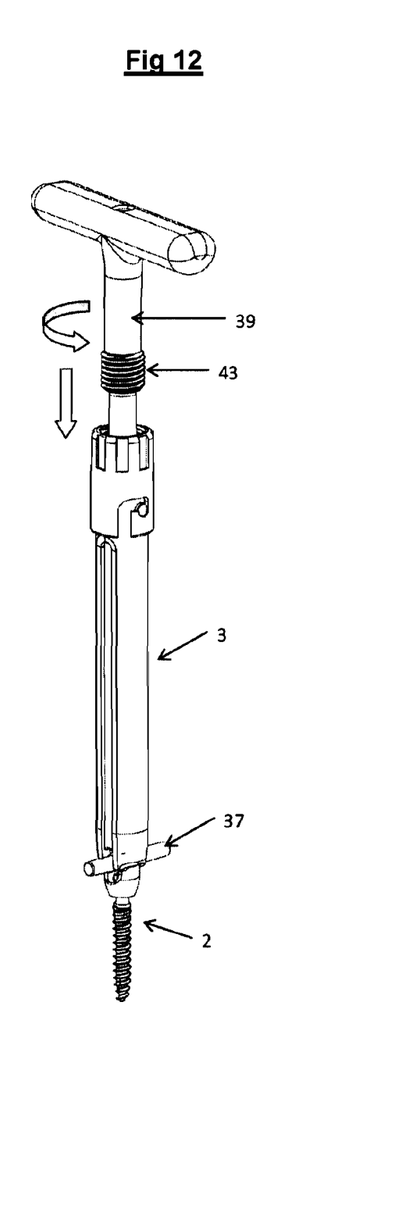

FIGS. 11 and 12 show the different operating steps involved in fitting in place the connecting rod element and the blocking element.

FIG. 11 shows two screw devices (2) with placement of the rod (37) in distal parts of the assembly tubes (3, 3'), which are advantageously situated outside the patient's wound above the skin, represented here by the line (P).

FIG. 12 shows the insertion of the rod (37) through two assembly tubes (3). This maneuver of lowering the rod is effected with the aid of the securing element (4).

A holding wing (39) with an external thread (43) is provided in order to increase the axial push that has to be exerted in order to engage the intervertebral connecting rod in the seat (25) of the head of the screw.

Figure 13:
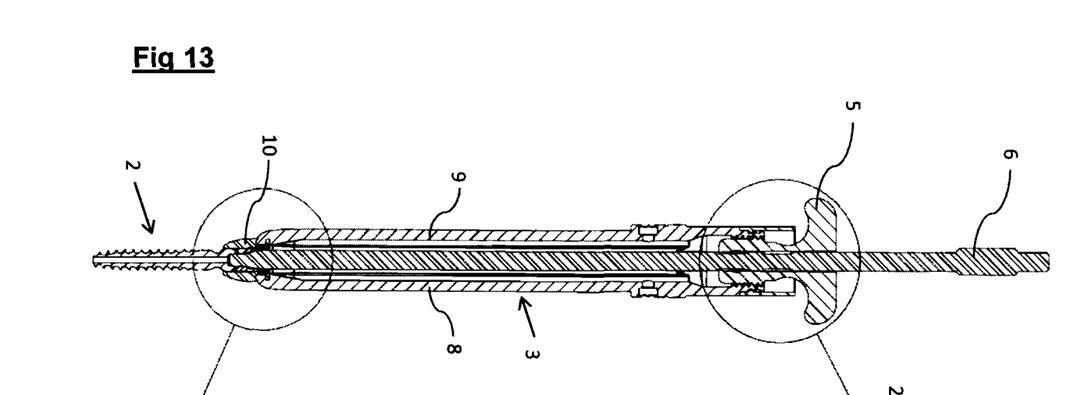
FIG. 13 shows a sectional view of the unit composed of screw/assembly tube/screwdriver.
Figure 15:
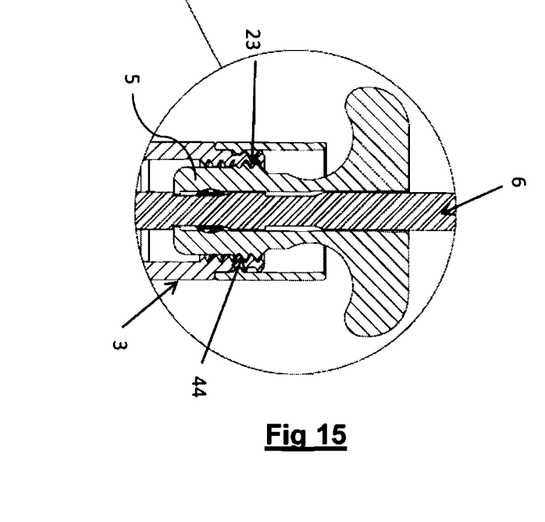

FIG. 13 shows a sectional view of the unit composed of screw, assembly tube and screwdriver, and FIGS. 14 and 15 show a detailed view of the proximal end and of the distal end, respectively, of the tube illustrated in FIG. 13.

The unit shown in FIG. 13 advantageously comprises a holding wing (5) for holding the screwdriver bar (6) in a given position with respect to the tube (3) and to the screw (2).

The T-shaped holding wing (5) is pre-mounted on the distal end of the tube (3). In its lower part, it has a thread (44) corresponding to the internal screw thread (23) of the distal part of the tube (3).

Advantageously, the holding wing (5) has, along its entire length, a channel through which the screwdriver bar (6) passes.

The holding wing (5) is designed to ensure an axial hold of the screwdriver bar (6) in the tube (3) while permitting a rotation movement of the bar inside the tube (3), this in order to allow the threaded part of the screw (2) to be driven in rotation, the head (10) of the screw (2) remaining fixed.

According to an advantageous embodiment, it is designed to maintain the alignment of the screwdriver bar (6) in the alignment of the bone-anchoring element (2).

Because of the factory pre-mounting of the screwdriver bar (6) on the screw, likewise pre-mounted in a tube (3), a reduced tolerance is permitted, and this ensures a better hold of the screw under bending forces.

Such pre-mounting also has the advantage of allowing time to be saved during surgery, since the procedure of placing the screwdriver bar on the bone-anchoring element is omitted, and of also limiting the surgical risk, since the duration of anesthesia is reduced.

Such pre-mounting also has the advantage of avoiding any problem of pairing between screwdriver bar and screw.

The invention claimed is:

1. A disposable surgical kit for fixing vertebrae using a posterior or postero-lateral route, said surgical kit comprising:
   at least one of a pedicle screw and a vertebral screw;
   an assembly tube cooperating with said at least one screw;
   said assembly tube being composed of two independent rigid half-shells;
   each of the half-shells having, on an inner face of a proximal end, a shoulder with a shape which complements a recess formed on each side of a screw head, in order to permit gripping or release of said at least one screw by spreading apart distal ends of said half-shells;
   a retractable securing element for securing said half-shells arranged to be placed in said assembly tube, said retractable securing element being retractable with respect to both half-shells; and
   said retractable securing element having longitudinal fastening means designed as a dovetail for engaging with complementary slides formed in said rigid half-shells.

2. A disposable surgical kit according to claim 1, wherein said assembly tube is pre-mounted securely on said at least one screw, the assembly tube being detachable from said at least one screw.

3. A disposable surgical kit according to claim 2, wherein said kit is supplied in a sealed package for sterile packaging containing said at least one screw which forms a bone-anchoring element and the pre-mounted assembly tube.

4. A disposable surgical kit according to claim 1, wherein the assembly tube has a longitudinal opening leading into a proximal part of said at least one screw which forms a bone-anchoring element for passage of a connecting element.

5. A disposable surgical kit according to claim 1, wherein said retractable securing element additionally has a blocking element for blocking a rod with respect to the at least one screw, and an internal diameter of the assembly tube permitting passage of the blocking element for blocking the rod on the at least one screw forming a bone-anchoring element.

6. The disposable surgical kit according to claim 1, further comprising an ancillary passing through the assembly tube and having an end pre-mounted on the at least one screw for transmission of a screwing torque.

7. The disposable surgical kit according to claim 1, wherein the two half-shells have, in their joined parts, tenon-and-mortise positioning means.

8. The disposable surgical kit according to claim 1, further comprising a ring provided with a bayonet-type formation for engaging stubs formed on the two half-shells.

9. The disposable surgical kit according to claim 8, wherein the securing element has an internal shape permitting passage of a screwdriver.

10. The disposable surgical kit according to claim 1, wherein all the components of the surgical kit are disposable.

* * * * *